(12) United States Patent
Kerr (10) Patent No.: US 12,226,518 B2
(45) Date of Patent: Feb. 18, 2025

(54) DENTAL POLISHING CUP

(71) Applicant: izzo, LLC, Plymouth Meeting, PA (US)

(72) Inventor: Sean H. Kerr, Wallingford, PA (US)

(73) Assignee: izzo, LLC, Plymouth Meeting, PA (US)

( * ) Notice: Subject to any disclaimer, the term of this patent is extended or adjusted under 35 U.S.C. 154(b) by 220 days.

(21) Appl. No.: 17/732,030

(22) Filed: Apr. 28, 2022

(65) Prior Publication Data

US 2022/0346921 A1    Nov. 3, 2022

Related U.S. Application Data

(60) Provisional application No. 63/282,480, filed on Nov. 23, 2021, provisional application No. 63/222,322,
(Continued)

(51) Int. Cl.
*A46B 13/02* (2006.01)
*A46B 3/00* (2006.01)
(Continued)

(52) U.S. Cl.
CPC .............. *A61K 8/965* (2013.01); *A46B 3/005* (2013.01); *A46B 5/0095* (2013.01); *A46B 9/005* (2013.01);
(Continued)

(58) Field of Classification Search
CPC ........ A61K 8/965; A61K 8/9789; A61K 8/19; A61K 8/21; A61K 8/24; A61K 8/25; A61K 8/29; A61K 8/345; A61K 2800/28; A61K 2800/87; A61K 2800/92; A46B 3/005; A46B 5/0095; A46B 9/005; A46B 13/02; A46B 2200/1066; A61C 3/06; A61C 17/005; A61Q 11/00
(Continued)

(56) References Cited

U.S. PATENT DOCUMENTS 3,727,315 A    4/1973  Spinello
5,316,475 A *  5/1994  Rosenberg ........... A61C 17/005
                                                      433/166
(Continued)

FOREIGN PATENT DOCUMENTS

CN    212118328 U    12/2020
CN    212118329 U    12/2020
(Continued)

OTHER PUBLICATIONS

Weihrauch Georg, Cleaning Brush, Especially a Toothbrush, WO 9952395 A1 (machine translation) (Year: 1999).*
(Continued)

*Primary Examiner* — Ralph A Lewis
*Assistant Examiner* — Mirayda A Aponte
(74) *Attorney, Agent, or Firm* — COZEN O'CONNOR (57) ABSTRACT

A dental polishing cup includes a body that defines a cup cavity for holding a dental treatment material, with the cup having an opening at its distal end. A portion of the body includes an enhanced-flexibility band (EFB) situated circumferentially at a certain distance from the distal end, the EFB providing a lesser stiffness of the body than other portions of the body that are situated lengthwise immediately distally and immediately proximately of the EFB.

19 Claims, 10 Drawing Sheets

Related U.S. Application Data filed on Jul. 15, 2021, provisional application No. 63/181,754, filed on Apr. 29, 2021, provisional application No. 63/181,735, filed on Apr. 29, 2021.

(51) Int. Cl.

| | |
|---|---|
| *A46B 5/00* | (2006.01) |
| *A46B 9/00* | (2006.01) |
| *A61C 3/06* | (2006.01) |
| *A61C 17/00* | (2006.01) |
| *A61K 8/19* | (2006.01) |
| *A61K 8/21* | (2006.01) |
| *A61K 8/24* | (2006.01) |
| *A61K 8/25* | (2006.01) |
| *A61K 8/29* | (2006.01) |
| *A61K 8/34* | (2006.01) |
| *A61K 8/96* | (2006.01) |
| *A61K 8/9789* | (2017.01) |
| *A61Q 11/00* | (2006.01) |

(52) U.S. Cl.
CPC ............... *A46B 13/02* (2013.01); *A61C 3/06* (2013.01); *A61C 17/005* (2013.01); *A61K 8/19* (2013.01); *A61K 8/21* (2013.01); *A61K 8/24* (2013.01); *A61K 8/25* (2013.01); *A61K 8/29* (2013.01); *A61K 8/345* (2013.01); *A61K 8/9789* (2017.08); *A61Q 11/00* (2013.01); *A46B 2200/1066* (2013.01); *A61K 2800/28* (2013.01); *A61K 2800/87* (2013.01); *A61K 2800/92* (2013.01)

(58) Field of Classification Search
USPC .................................................. 433/125, 166
See application file for complete search history.

(56) References Cited

U.S. PATENT DOCUMENTS

| | | | | |
|---|---|---|---|---|
| 5,797,744 | A * | 8/1998 | Rosenberg | ........... A61C 17/005 |
| | | | | 433/166 |
| 2012/0034575 | A1 | 2/2012 | Tarr | |
| 2016/0228341 | A1 | 8/2016 | Lucas et al. | |
| 2016/0331495 | A1 | 11/2016 | Shokoohi | |
| 2017/0202652 | A1 | 7/2017 | Wang et al. | |

FOREIGN PATENT DOCUMENTS

| | | | |
|---|---|---|---|
| WO | 2014185884 | A1 | 11/2014 |
| WO | WO 2021/067872 | | 4/2021 |

OTHER PUBLICATIONS

Search Report with Written Opinion dated Jul. 27, 2022 issued in International Patent Application PCT/US22/27003.

Office Action dated Oct. 8, 2024, issued in U.S. Appl. No. 17/732,147, 14 pages.

Supplementary European Search Report dated Dec. 17, 2024, issued in corresponding EP Application No. 22796825.2.

* cited by examiner

*FIG. 11* dental POLISHING CUP

PRIOR APPLICATIONS

This application claims the benefit of U.S. Provisional Applications No. 63/181,735 filed Apr. 29, 2021, 63/181,754 filed Apr. 29, 2021, 63/222,322 filed Jul. 15, 2021, and 63/282,480 filed Nov. 23, 2021, which are incorporated by reference into the present disclosure. This application is generally related to, and filed concurrently with, co-pending U.S. patent application Ser. No. 17/732,147, filed Apr. 28, 2022, entitled "MESO-ABRASIVE DENTIFRICE AND SYSTEM FOR USING SAME" which is also incorporated by reference herein.

FIELD OF THE INVENTION

The invention relates generally to dental tools or instruments and, more particularly, to devices for cleaning or polishing teeth.

BACKGROUND OF THE INVENTION

Coronal polishing is a procedure used to remove stain and plaque from the enamel surfaces of the teeth after the removal of hard deposits such as calculus from the tooth surfaces. A polishing procedure is typically performed by a dental professional as a part of a routine dental visit. The process involves the use of a polishing agent that is applied to the teeth using a polishing cup. The polishing cup is typically made from an elastomer, such as a natural or synthetic rubber compound and is shaped to hold the polishing agent against the working surface while the cup is rotated by a motor. The polishing cup is removably coupled to a dental handpiece which is handled by a dental hygienist or other dental clinician. The handpiece contains a motor or a mechanical linkage that is, in turn, coupled to a motor by a flexible drive shaft or other suitable coupling.

In a coronal polishing procedure, the clinician maintains the cup at a right angle (i.e., normal) to the surface of the tooth. It has been established that the tooth structure can be damaged if the cup is held on the tooth at an off-axis angle. If a typical polishing cup is applied against a tooth off-axis, only the outer edge of the cup will maintain contact with the tooth. This will reduce the amount of the cup area that is contacting the tooth and thus significantly increase the local pressure on the contact area of the tooth. This is especially problematic when the edge of the cup contacts the softer dentin structure of the tooth.

Another issue with off-axis application of the polishing cup is that the user, especially if they are lacking professional training or are performing the polishing themselves, is typically not aware that the cup is not properly contacting the working surface and thus not effectively cleaning all areas of the tooth. It is difficult to maintain the cup at a nearly 90-degree angle to the tooth at all times. First, the surfaces of the tooth are highly contoured and vary from tooth to tooth. Thus, the clinician must constantly change their hand position to maintain this contact angle. This is not only difficult given the practical time constraints allocated the procedure, but the constant repositioning of the dental handpiece can lead to musculoskeletal problems for the clinician, such as carpal tunnel and cubital tunnel syndrome. Secondly, certain angles are hard to reach given the relatively small size of the oral cavity and soft tissues.

A practical solution is needed to these, and related, challenges associated with the use of dental polishing cups.

SUMMARY OF THE INVENTION

According to some aspects of this disclosure, a dental polishing cup comprises a body formed from an elastic material. The body has a length along a longitudinal axis, a proximal end, a distal end, and a round cross-section taken perpendicularly to the length. The body has a distal diameter at the distal end, which further defines a cup cavity with an opening at the distal end. A portion of the body includes an enhanced-flexibility band (EFB) situated circumferentially at a certain distance from the distal end, the EFB providing a lesser stiffness of the body than other portions of the body that are situated lengthwise immediately distally and immediately proximately of the EFB.

Advantageously, the EFB may facilitate articulation, contourability, and flaring of the polishing cup in response to applied forces along the longitudinal axis and also along an off-center axis that is offset from the longitudinal axis.

According to another aspect of this disclosure a dental kit comprises a power handle, a polishing cup, and a polishing paste. The polishing cup has a body comprising an elastic material, a length along a longitudinal axis, a proximal end, a distal end, and a round cross-section taken perpendicularly to the length and wherein the body has a distal diameter at the distal end, and defines a cup cavity for the polishing paste, with an opening at the distal end. A portion of the body includes an enhanced-flexibility band (EFB) situated circumferentially at a certain distance from the distal end, the EFB providing a lesser stiffness of the body than other portions of the body that are situated lengthwise immediately distally and immediately proximately of the EFB.

According to another aspect of the disclosure, dental kit has one or more of a charging unit, a brush head, a power supply, a scaler tool, a sanitizer unit, and a charging cradle.

A number of other advantages will become apparent from the following Detailed Description.

BRIEF DESCRIPTION OF THE DRAWINGS

The invention may be more completely understood in consideration of the following detailed description of various embodiments of the invention in connection with the accompanying drawings (which may not be drawn to scale).

DETAILED DESCRIPTION OF THE PRESENTLY PREFERRED EMBODIMENTS

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

In the following description, certain specific details are set forth in order to provide a thorough understanding of various disclosed embodiments. However, one skilled in the relevant art will recognize that embodiments may be practiced without one or more of these specific details, or with other methods, components, materials, etc.

Reference throughout this specification to "an embodiment," "one embodiment," "one implementation," "one aspect," or "an implementation" means that a particular feature, structure or characteristic described in connection with the implementation is included in at least one implementation. Thus, the appearances of the phrases "in one implementation", "in an implementation," "in one aspect," "in an example," "in an embodiment," or the like, in various places throughout this specification are not necessarily all referring to the same implementation. Furthermore, the particular features, structures, or characteristics may be combined in any suitable manner in one or more implementations.

Unless the context requires otherwise, throughout the specification and claims that follow, the word "comprising" or "comprises" is synonymous with "including" or "includes" and is inclusive or open-ended (i.e., does not exclude additional, unrecited elements or method acts).

As used in this specification and the appended claims, the singular forms "a," "an," and "the" include plural referents unless the content clearly dictates otherwise. It should also be noted that the term "or" is generally employed in its inclusive-or sense (i.e., "and/or"), unless an exclusive-or interpretation is expressly and unambiguously set forth.

Approximations such as "about," "approximately," "substantially," "near," "proximate," "essentially," or the like, when used in connection with a relationship or a state value, are to be interpreted as clear and definite, with an ascribed meaning equal to the absolute relationship or exact value as stated, with a permissible tolerance or variation that does not depart from the structure, form, fit, or function of the thing described, unless a different and definite meaning is provided expressly or contextually.

Reference throughout this specification to a "clinician" extends beyond those formally trained in the dental sciences but also includes any person who is using the device, including a consumer performing this procedure on their own or performing it for someone they are caring.

The headings and Abstract of the Disclosure provided herein are for convenience only and do not interpret the scope or meaning of the embodiments.

Figure 1:
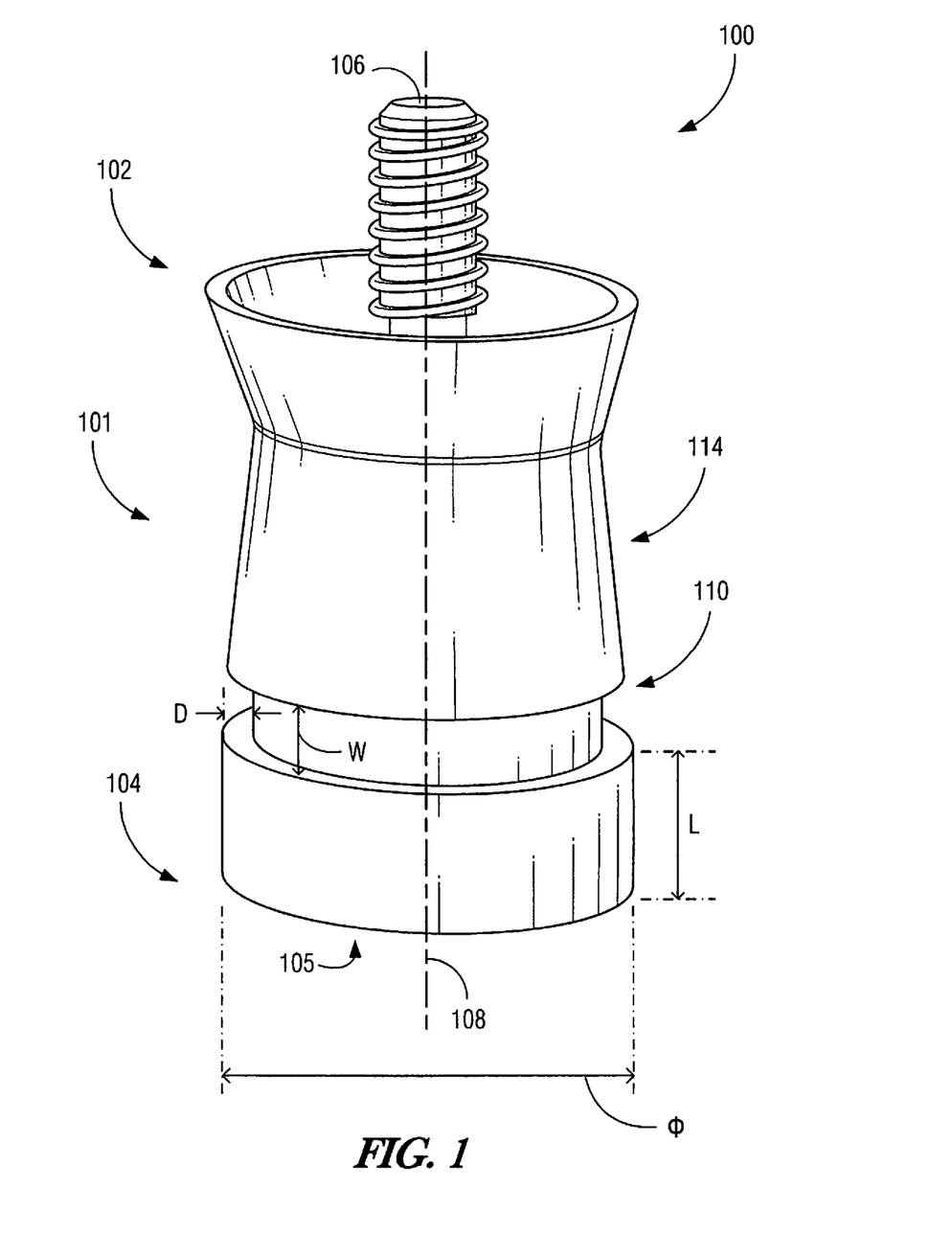
FIG. 1 is a perspective-view diagram illustrating an example of a dental polishing cup according to an aspect of the disclosure.

FIG. 1 is a perspective-view diagram illustrating an example of a dental polishing cup 100 according to an aspect of the disclosure. Polishing cup 100 has a generally cylindrical, frusto-conical, or compound (as shown) body 101 having distal cup diameter Φ with proximal end 102 and distal end 104. Body 101 of polishing cup 100, as shown, has a round cross-section (taken perpendicularly to its length at any point), even though its diameter at any point along its length may vary.

Body 101 may be formed from any suitable material having desired mechanical properties of flexibility, resilience, elasticity, hardness, etc., for the polishing application, and which is also safe for contact with oral tissue, including teeth, gums, etc. An elastomeric material may be utilized, such as natural and synthetic rubbers, silicone elastomers, nitrile rubbers, ethylene propylene diene rubbers, neoprene rubbers, thermoplastic elastomers, or combinations thereof (e.g., such as materials that may be co-molded or attached to form a composite elastomeric body 101). Typical hardness may be in the range of 40-70 Shore A but may extend to 20-90 Shore A in certain embodiments. Body 101 defines a cup cavity 105 with opening at distal end 104 into which a dental treatment material such as a polishing agent (e.g., an abrasive paste, etc.), may be located. Cup cavity 105 may contain baffles, partial walls, ribs, grooves, webbing, bumps, or other structures (not shown) to facilitate retention of the polishing agent or enhance the polishing performance. The outer surface of the cup may also contain ribs, grooves, bumps, or other structures (not shown) to enhance cleaning, promote flexibility or reduce splatter from fluids in the oral cavity. The walls of body 101 may have varying thicknesses along the longitudinal axis 108. For instance, the wall thickness may be greater near proximal end 102, and may be progressively thinner approaching distal end 104.

Fastener 106 is situated at proximal end 102 and facilitates connecting polishing cup 100 to a working end of a dental handpiece (not shown). The cup can also be fastened to a handpiece or disposable Prophy angle with other features, including but not limited to, snaps and over-molding. In operation, the working end of the dental handpiece rotates polishing cup 100 about its longitudinal axis 108. Rotation may be unidirectional, bidirectional, or oscillatory.

Fastener 106 may be formed from the material of body 101, or it may be made from a different material (e.g., thermoplastic, metal, etc.) and affixed to body 101 such as by adhesive, compression, friction, treading, swaging, overmolding, or otherwise. Fastener 106 may be protruding from body 101, or it may be recessed within body 101. In the example depicted, fastener 106 comprises a protruding threaded shaft. In other implementations other types of fasteners may be utilized, such as a threaded bore, an unthreaded shaft, a shaft with a hexagonal cross-section, a socket-type connector, a compression-fit connector, a snap-fit connector, hook-and-loop or inter-meshing fasteners, adhesive fasteners, or the like, or some combination of such connectors.

Body 101 of polishing cup 100 has an exterior surface 114. Body 101 further includes an enhanced-flexibility band (EFB) 110 situated circumferentially along a portion of body 101. In the example depicted in FIG. 1, EFB 110 is implemented as an annular groove in the wall of body 101. Annular-groove EFB 110 has a width W along the length dimension, and a depth D along the radial dimension. It is positioned lengthwise at distance L from distal end 104. In this implementation, EFB 110, in effect, is a reduced wall thickness in a portion of body 101, compared to portions of the body wall situated immediately proximately and immediately distally of the EFB. EFB 110 facilitates articulation, contourability, and flaring of polishing cup 100 in response to applied forces to provide a greater contact surface of the cup with the working surface (e.g., a tooth), compared to a similar polishing cup without EFB 110. An example of applied force in a human tooth-polishing application is about 150 g.

In various embodiments, distal diameter Φ may be selected to suit the application. For instance, various polishing cup sizes may be offered for use in pediatric or adult patients. Likewise, various polishing cup sizes may be offered for different veterinary applications. As one example for general use on human teeth, a polishing cup with a distal diameter Φ of 6.35 mm may be used.

The distance L of EFB 110 from distal end 104 may be selected to suit the application. In some embodiments, the EFB distance L is selected as a ratio r of cup diameter Φ such that $$L = r\Phi.$$

Preferably, r is selected to be no greater than 0.7. The width W of EFB 110 may be selected according to desired performance characteristic. In the example as depicted in FIG. 1, the width W of annular-groove EFB 110 is about 0.8 mm. The depth D of annular-groove EFB 110 may likewise be selected to suit the desired performance characteristics. In the example shown in FIG. 1, the depth D is about 0.675 mm.

Figure 2A:
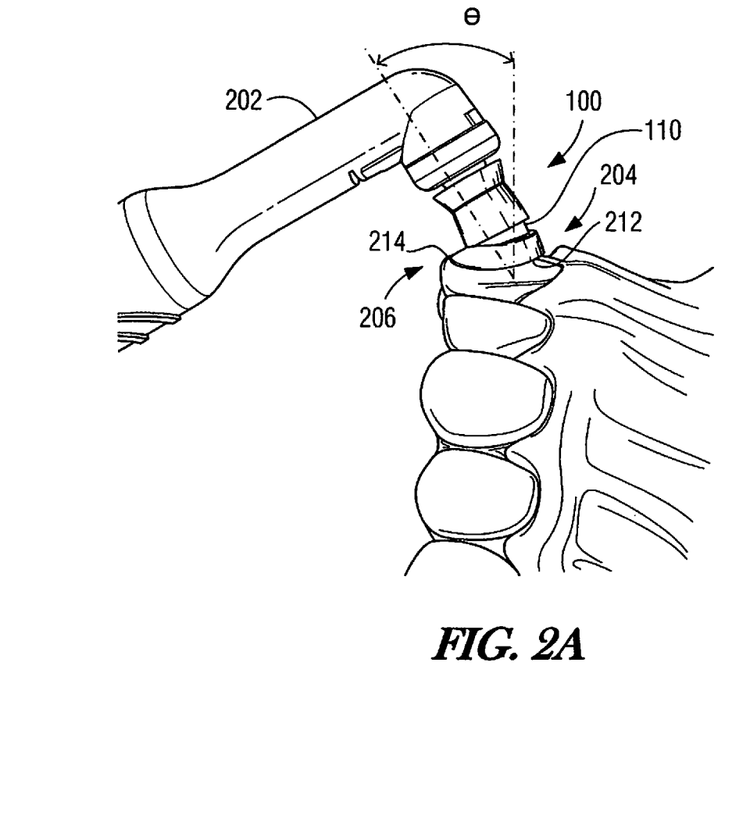
FIG. 2A is a diagram illustrating certain off-axis performance characteristics of a polishing cup having an EFB according to an embodiment.
Figure 2B:
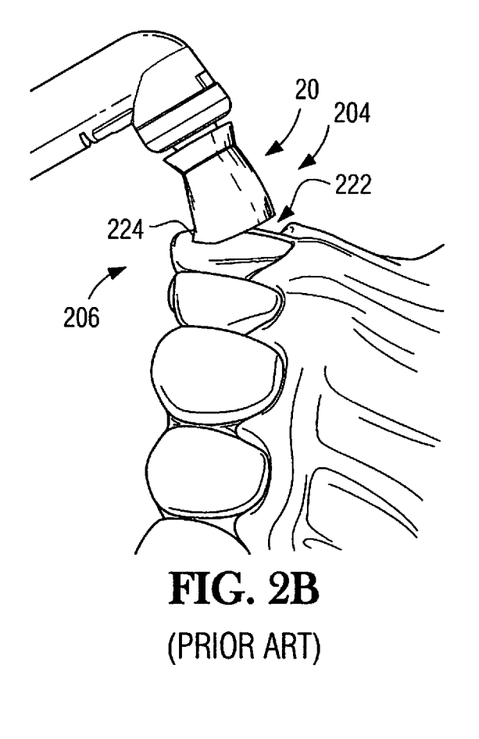
FIG. 2B is a diagram illustrating a conventional polishing cup without an EFB, according to the prior art.

FIGS. 2A-2B are diagrams illustrating certain off-axis performance characteristics of a polishing cup having an EFB according to an embodiment of the invention, and a conventional polishing cup without an EFB, respectively. As depicted in FIG. 2A, polishing cup 100 (having EFB 110) is attached to dental handpiece 202, and engaged with a working surface (e.g., a tooth). The engagement of polishing cup 100 with the working surface is off-center by angle θ as shown. As a result, there is non-uniform force applied by polishing cup 100 across the working surface: there is a lower-force side 204, and a higher-force side 206. Notably, polishing cup 100 makes contact 212 with the working surface at lower-force side 204. Likewise, polishing cup 100 makes contact 214 with the working surface at high-force side 206. This articulation performance is achieved by flexing of polishing cup 100 that is facilitated by elastic deformation of polishing cup 100, particularly, at the EFB 110 as shown. In addition, at higher-force side 206, the distal end of polishing cup 100 is significantly flared at contact point 214, thereby distributing the force of contact between polishing cup 100 and the working surface over a greater interfacial surface area.

By comparison, as shown in FIG. 2B, conventional polishing cup 20, having less flexibility without an EFB, contact between polishing cup 20 and the working surface is lost at lower-force side 222, due to lifting of the distal end of polishing cup 20 on that side. Also, due to the relatively less flexible body of conventional polishing cup 20, at the higher-force side 206, the contact force is concentrated at contact point 224 with comparatively minimal flaring of the distal end of conventional polishing cup 20.

Figure 3A:
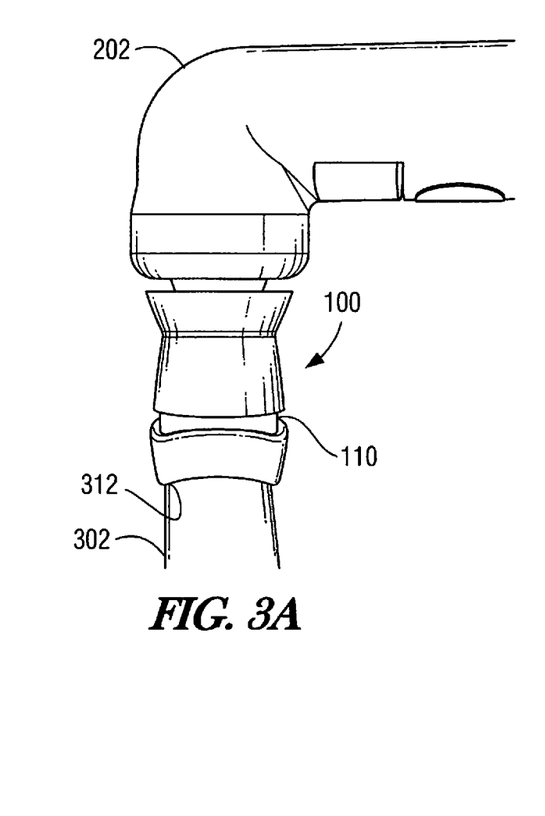
FIG. 3A is a diagram illustrating performance characteristics of a polishing cup having an EFB according to an embodiment.
Figure 3B:
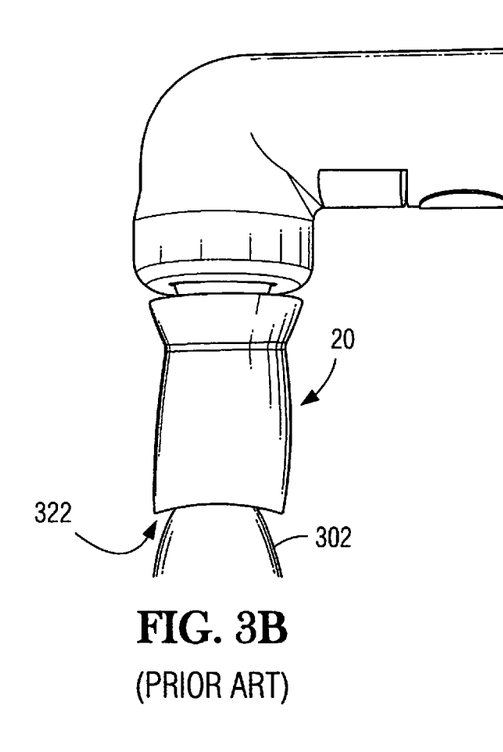
FIG. 3B is a diagram illustrating a conventional polishing cup without an EFB in a convex-curved working-surface application, according to the prior art.

FIGS. 3A-3B are diagrams illustrating performance characteristics of a polishing cup having an EFB according to an embodiment of the invention, and a conventional polishing cup without an EFB, respectively, in a convex-curved working-surface application. As depicted in FIG. 3A, polishing cup 100 having an EFB is pressed onto curved working surface 302 which has a tight radius relative to the distal cup diameter. In the example depicted, working surface 302 has a radius of 2.4 mm, which is equal a ratio of 0.38 distal diameter. EFB 110 permits the distal end of polishing cup 100 to curve and warp to maintain intimate contact with convex-curved working surface 302, as indicated at 312. In other words, contact is maintained along the entire circumference of the distal end. Hence, polishing cup with EFB 100 may advantageously adapt to variations in dentition. This is especially advantageous for allowing polishing cup 100 to reach the interproximal areas. According to various related embodiments, polishing cup 100 is formed with such dimensions that it conforms around a convex surface having a radius of curvature that is between 0.45 and 0.38 times the distal diameter Φ.

By comparison, as shown in FIG. 3B, conventional polishing cup 20 does not conform to curved working surface 302, as indicated at 322, with equivalent force applied as in the demonstrated example depicted in FIG. 3A.

Figure 4A:
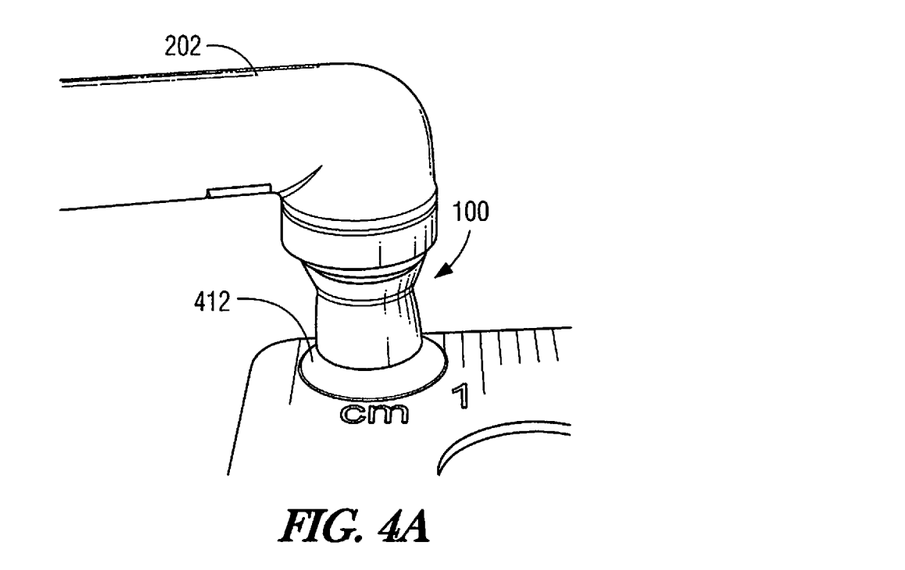
FIG. 4A is a diagram illustrating flaring performance characteristics of a polishing cup having an EFB according to an embodiment.
Figure 4B:
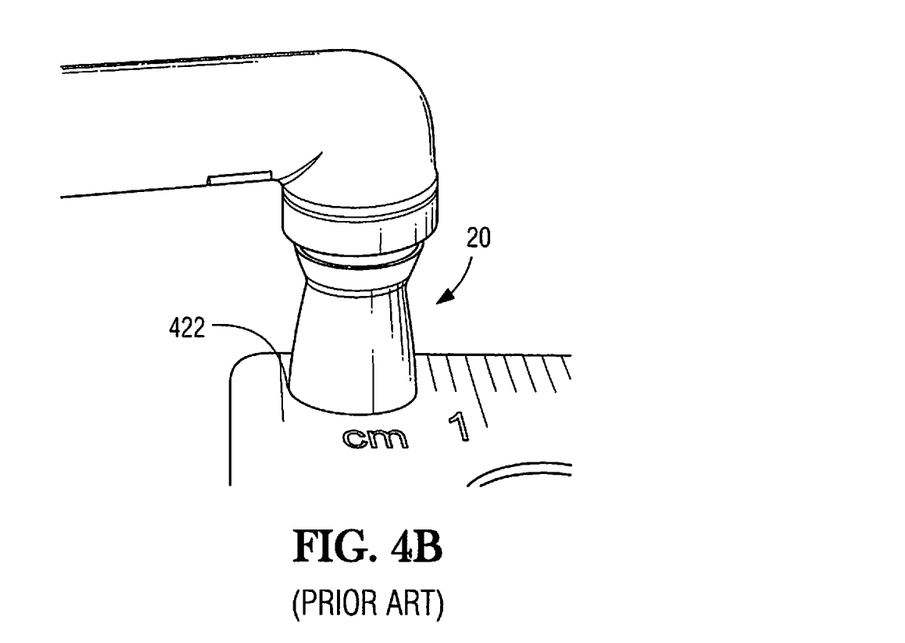
FIG. 4B is a diagram illustrating a conventional polishing cup without an EFB when the polishing cups are pressed against a surface, according to the prior art.

FIGS. 4A-4B are diagrams illustrating flaring performance characteristics of a polishing cup having an EFB according to an embodiment of the invention, and a conventional polishing cup without an EFB, respectively, when the polishing cups are pressed against a surface. This ability to flare is sought after by the clinicians since it allows the cup to better access interproximal areas and reach the gingival and subgingival margin. As shown in FIG. 4A, polishing cup 100, which has an EFB as discussed above, and which has a nominal distal diameter Φ of about 6.35 mm, flares out to a diameter of about 8.5 mm, under an applied pressure of 150 g as depicted at 412. This is a flaring amount of 33%. In other embodiments, where the material of body 101 of polishing cup 100 is stiffer, where the wall thickness is greater, or where the EFB is narrower or less deep, the flaring amount may be commensurately smaller. For instance, in various examples, the flaring amount may be 15%, 20%, or 25%.

By comparison, as depicted in FIG. 4B, conventional polishing cup 20, also having a nominal distal diameter of 6.35 mm flares out to only around 7 mm under the same applied force (e.g., 150 g), depicted at 422. This demonstrated performance comparison shows an improved flaring ability of 330% for polishing cup 100 over conventional polishing cup 20.

Figure 5:
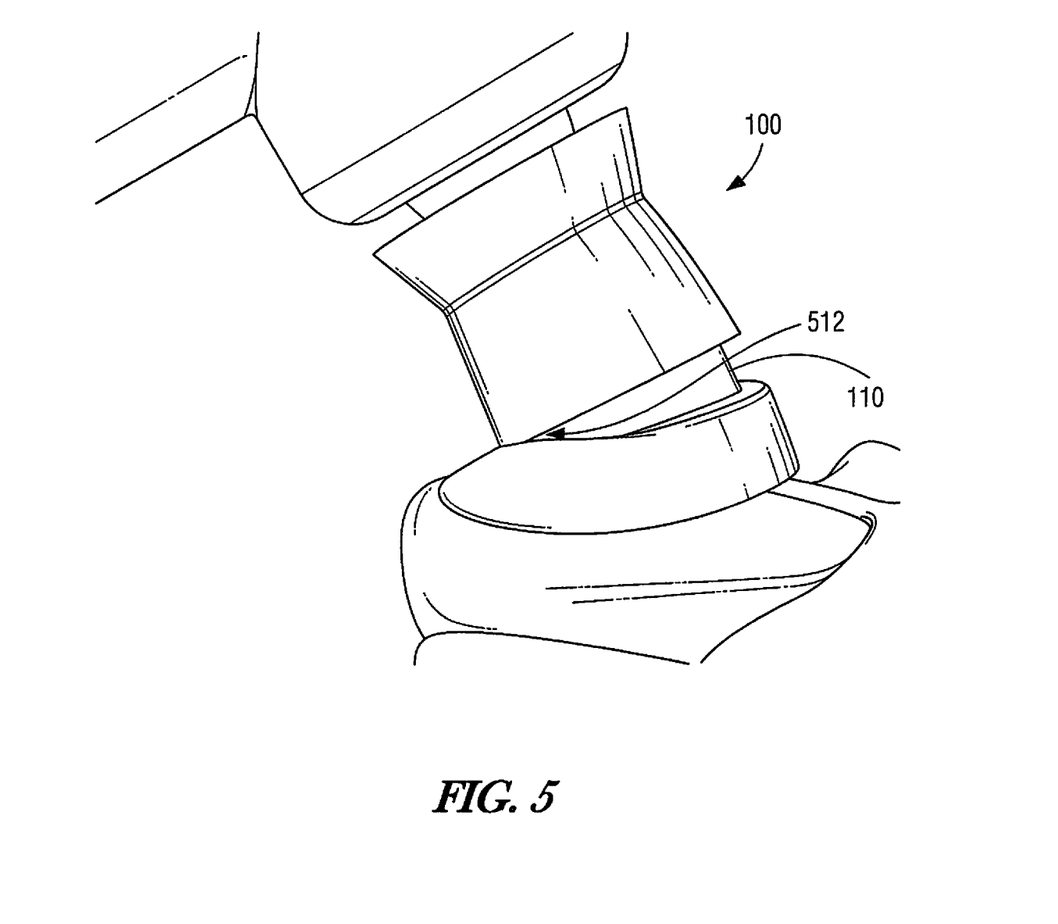
FIG. 5 is a diagram illustrating an additional aspect of off-axis performance of polishing cup having an EFB according to some embodiments.

FIG. 5 is a diagram illustrating an additional aspect of off-axis performance of polishing cup 100 having EFB 110, according to some embodiments. In this example, EFB 110 is sized to provide a limit to the articulation of polishing cup 100 while an off-axis force is applied. As shown, EFB 110 closes at a specific angle 512. This closed-EFB condition results in increased stiffness of polishing cup 100 at sufficiently-large off-axis angles. This feature can be used to provide increased stiffness when needed by the clinician to achieve a concentrated polishing effect. Various combinations of groove depths D and widths W may be selected to achieve desired EFB-closing performance.

As discussed above, variations of the features shown and described are contemplated as various related embodiments. For instance, the geometry of an EFB which is in the form of an annular groove may be varied. In other implementations, an EFB may have a different geometry or material composition. By way of example and not limitation, some examples of such variations and additional embodiments are described below.

Figure 6A:
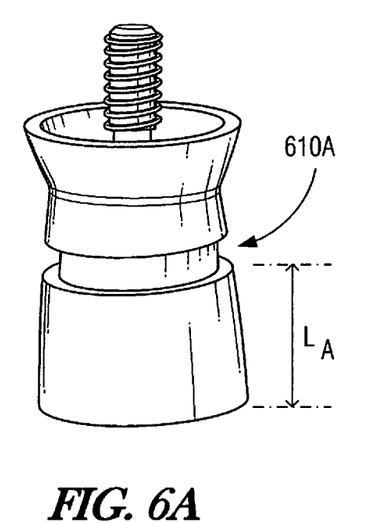
FIG. 6A illustrates a polishing cup with the EFB at a first position along the length of the cup, in an embodiment.
Figure 6B:
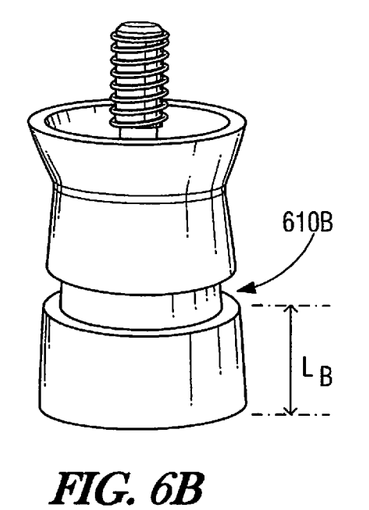
FIG. 6B illustrates a polishing cup with the EFB at a second position along the length of the cup, in an embodiment.
Figure 6C:
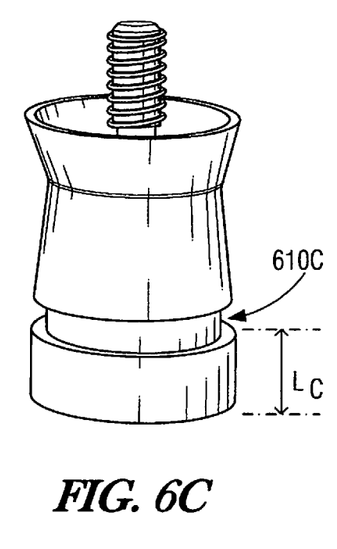
FIG. 6C illustrates a polishing cup with the EFB at a third position along the length of the cup, in an embodiment.

With reference to the basic geometry of annular-groove EFB 110 as depicted in FIGS. 1-5, Table 1 provides examples of ratio r (corresponding to the distance L of the EFB as a length from the distal end to the distal diameter Φ) according to various embodiments. For illustration, these examples are depicted in FIGS. 6A-6C with various annular-groove EFBs 610A, 610B, and 610C shown having positions $L_A$, $L_B$, and $L_C$, respectively.

TABLE 1

| General Description of EFB Distance L | r |
|---|---|
| Proximal ($L_A$) | 0.70 |
| Mid ($L_B$) | 0.55 |
| Distal ($L_C$) | 0.40 |

The depth D of annular-groove EFB 110 may likewise be selected to suit the desired performance characteristics. For instance, Table 2 provides various examples of groove depth D, each of which may be suitable for use with a polishing cup having a distal diameter Φ of 6.35 mm:

TABLE 2

| General Description of EFB Annular Groove | D (mm) |
|---|---|
| Shallow | 0.57 |
| Mid | 0.67 |
| Deep | 0.78 |

Notably, in each of these embodiments, the annular-groove EFB provides a band of narrower wall thickness than the wall thicknesses immediately proximally, and immediately distally of the EFB.

The following graph shows a comparison of off-axis tolerance to groove location and depth. Notably, the more distally located the groove yields a larger off-axis angle (See FIG. 11).

Figure 11:
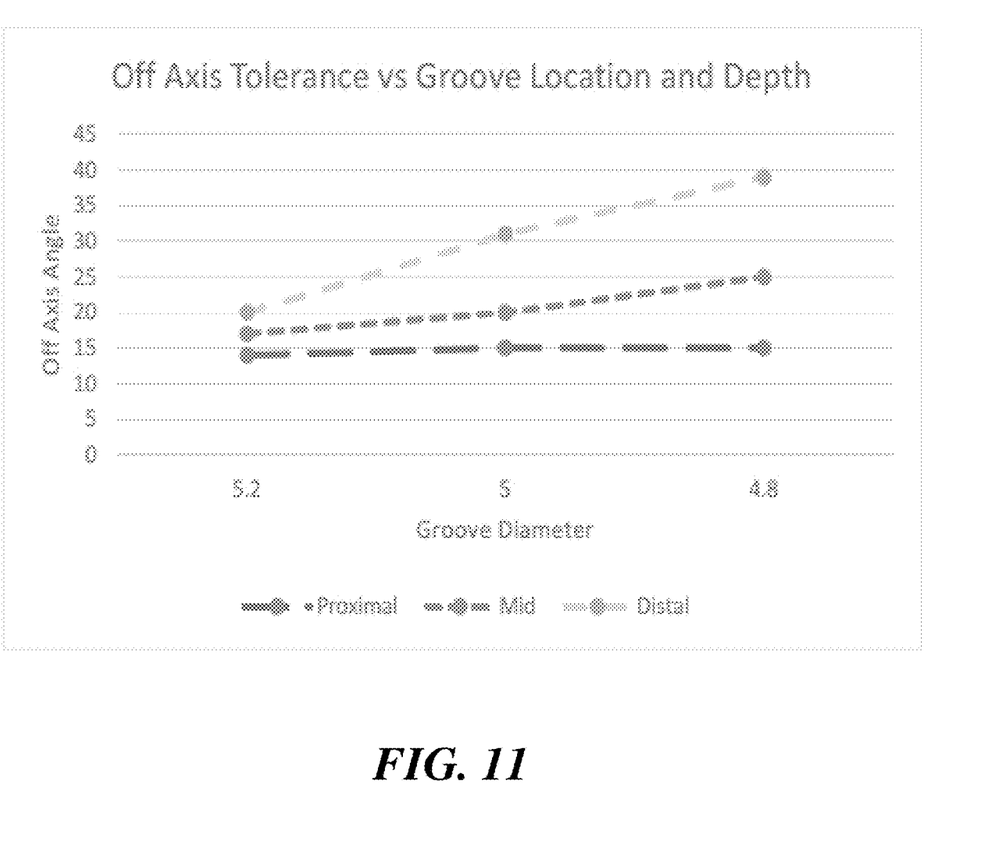
FIG. 11 is a graph showing a comparison of off-axis tolerance to groove location and depth.

The off angle tolerance is defined as the number of degrees (from 90 degrees) that the cup can articulate before it no longer completely contacts the tooth. A higher number indicates that the cup can articulate more. The off angle tolerance for the control cup was 14 degrees.

Figure 7A:
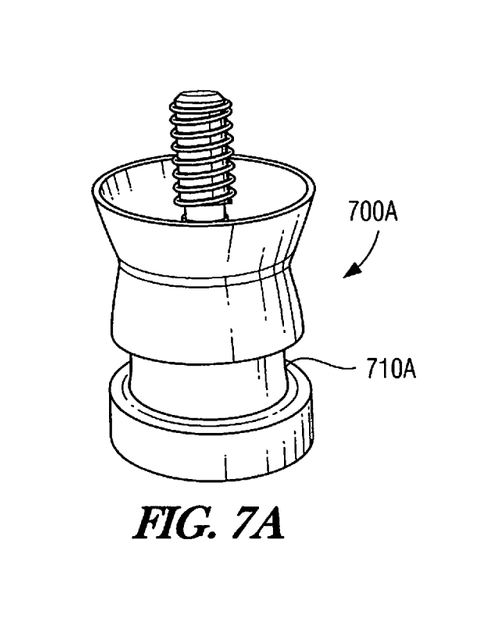
FIG. 7A illustrates a polishing cup with wall profile of a groove-type EFB having a first width, according to an embodiment.
Figure 7B:
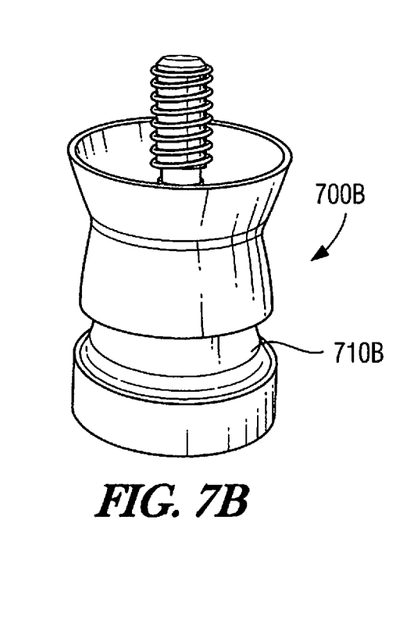
FIG. 7B illustrates a polishing cup with wall profile of a groove-type EFB having a second width, according to an embodiment.
Figure 7C:
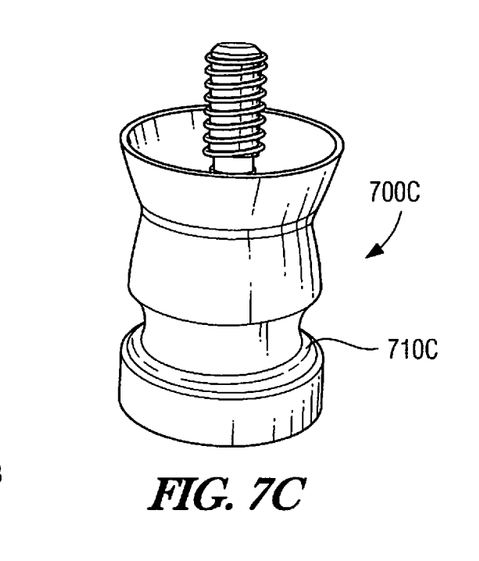
FIG. 7C illustrates a polishing cup with wall profile of a groove-type EFB having a third width, according to an embodiment.

As another type of variation of the annular-groove EFB, the groove width W may be varied. As discussed above, variation of the groove width W, whether by itself, or in combination with variation of the groove depth D along the radial direction, can be achieved by product designers to tune the desired performance parameters of the polishing cup and provide variations in flexibility for articulation, flaring, convex-surface contouring, and flex-limiting (i.e., "closing"). FIGS. 7A-7C illustrate variations in width, and wall profile of a groove-type EFB according to several related embodiments. As shown in FIG. 7A, Polishing cub 700A has annular-groove EFB 710A that is relatively wider, e.g., W=1 mm to 3 mm, than EFB 110 depicted in FIG. 1.

As a related type of variation, the wall profile of the groove-type EFB may be specially formed to meet certain performance specifications. In the example of FIG. 7B, polishing cup 700B has EFB 710B with a tapered wall at one or both ends of the band. Likewise, as shown in FIG. 7C, polishing cup 700C has EFB 710C with a contoured wall as shown. The contour may be curved, tapered, or stepped as various examples, to provide a desired flexibility of the respective polishing cup.

Figure 8:
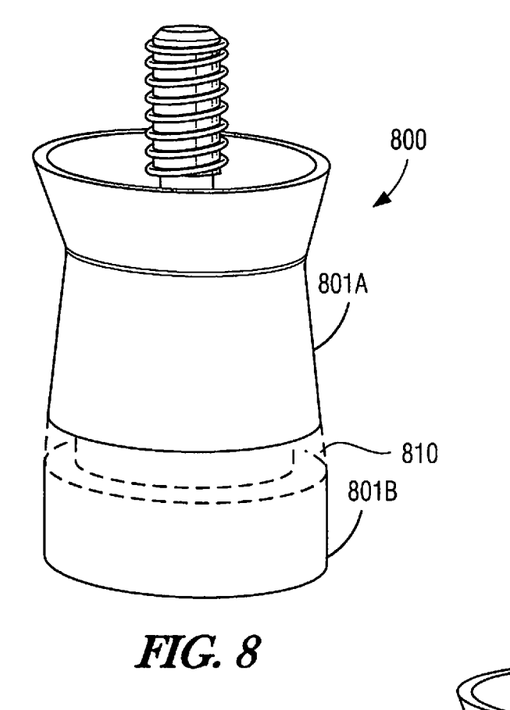
FIG. 8 illustrates a type of EFB that may be implemented using a plurality of different materials in the construction of the polishing according to some embodiments.

FIG. 8 illustrates a different type of EFB, using a plurality of different materials in the construction of the polishing cup rather than a groove. As shown, polishing cup 800 has multiple body portions, which include proximal body portion 801A, distal body portion 801B, and EFB portion 810. Proximal and distal body portions 801 may be formed from one or more relatively harder material(s); whereas EFB portion 810 is formed from a relatively softer or compressible material (e.g., foam, softer elastomer, or the like). EFB portion 810 may be co-molded, welded, adhesively coupled, or otherwise attached, with the adjacent body portions. In this type of EFB, the wall thickness is not necessarily different in the EFB region; however, the flexibility of the overall polishing cup 800 is nonetheless enhanced by virtue of the softer EFB material. Hence, in this type of embodiment, the EFB provides a band of material which has a lesser stiffness (i.e., greater pliability) than the polishing-cup body portions immediately proximally, and immediately distally of the EFB.

Figure 9:
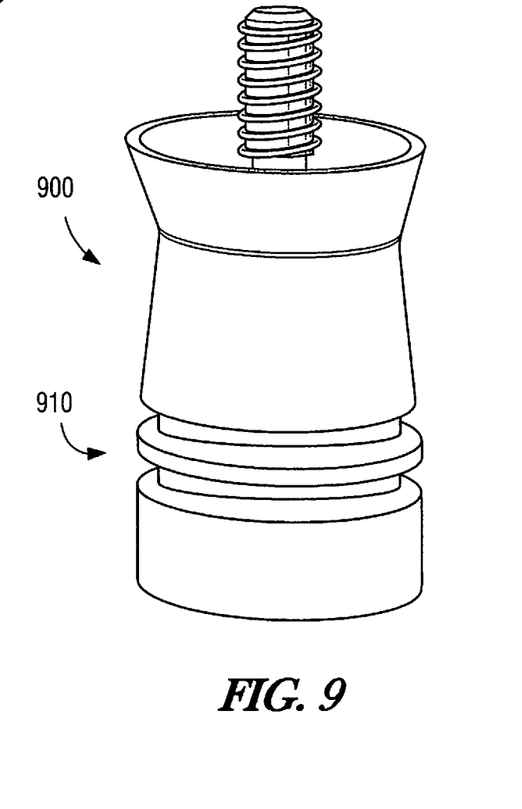
FIG. 9 is a diagram illustrating another type of embodiment, in which a polishing cup has an EFB that comprises a plurality of circumferential grooves.

FIG. 9 is a diagram illustrating another type of embodiment, in which polishing cup 900 has EFB 910 that comprises a plurality of grooves as shown. In related embodiments, other structures of EFB may be employed. For instance, an EFB may have varying (e.g., undulating) widths W around the circumference of the polishing cup. In other examples, the EFB may be formed as a set of perforations, portals or cutouts around the circumference to achieve substantially equivalent one or more performance characteristics as described above.

It should be apparent from the description above that an improved polishing cup utilizing an EFB according to one or more of the embodiments described above would offer a number of advantages to dental professionals. Moreover, a polishing cup in accordance with one or more of the embodiments described above may be well-suited for users who are not a clinicians or trained dental professionals to perform tooth polishing on themselves. For instance, the improved off-axis performance means that the user does not have to hold the polishing cup at a nearly-perpendicular angle to the tooth to achieve safe and effective polishing. A novice user who is trying to manipulate the device through a mirror (as opposed to direct sight) tends to have difficulty maintaining a right angle to the tooth surface at all times as is typically called for with the use of conventional polishing cups. Accordingly, embodiments of the present subject matter may be particularly advantageous as part of a consumer self-care product or kit.

Figure 10:
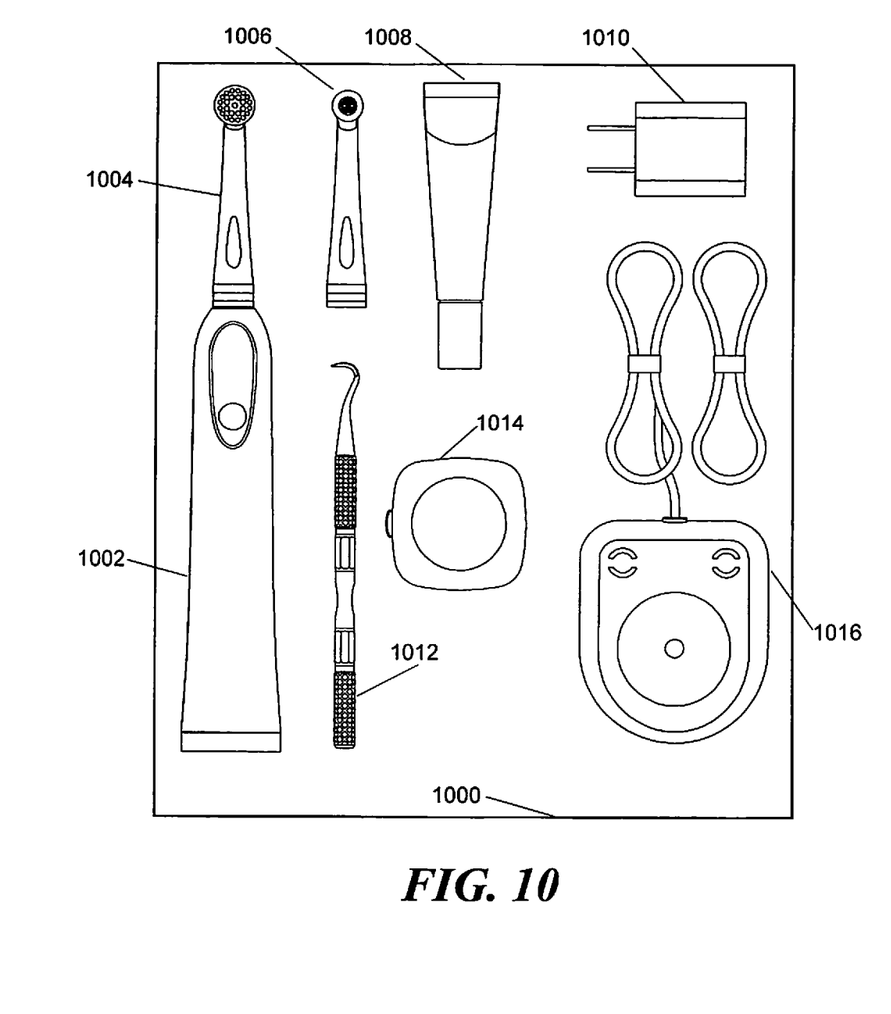
FIG. 10 is a diagram illustrating an example of a consumer self-care kit according to an embodiment.

FIG. 10 is a diagram illustrating an example of a consumer self-care kit 1000 according to an embodiment. Kit 1000 includes a power handle 1002 for an oscillating toothbrush. Power handle 1002 comprises a motor, mechanical couplings, a battery, a charging circuit, a controller, one or more indicators (e.g., LED lights), and one or more inputs or sensors, such as a pushbutton, load sensor, or the like. Kit 1000 further includes brush head 1004, and polishing cup head 1006 comprising a polishing cup in accordance with one or more of the embodiments described above. Kit 1000 further includes polishing paste 1008, AC/DC power supply 1010, scaler tool 1012, ultraviolet sanitizer unit 1014, and charging cradle 1016.

ADDITIONAL NOTES AND EXAMPLES

Example 1 is a dental polishing cup, comprising: a body comprising an elastic material, the body having a length along a longitudinal axis, a proximal end, a distal end, and a round cross-section taken perpendicularly to the length, wherein the body has a distal diameter at the distal end, and the body further defines a cup cavity with an opening at the distal end; and wherein a portion of the body includes, an enhanced-flexibility band (EFB) situated circumferentially at a certain distance from the distal end, the EFB providing a lesser stiffness of the body than other portions of the body that are situated lengthwise immediately distally and immediately proximately of the EFB.

In Example 2, the subject matter of Example 1 includes, wherein the body comprises a circumferential wall having a certain wall thickness any given point along the length, and wherein the EFB has a reduced wall thickness than the other portions of the body that are situated lengthwise immediately distally and immediately proximately of the EFB.

In Example 3, the subject matter of Examples 1-2 includes, wherein the EFB is defined by the body as a circumferential groove having a certain depth along a radial direction.

In Example 4, the subject matter of Example 3 includes, wherein the depth along the radial direction is in the range from about 0.5 mm through about 0.8 mm.

In Example 5, the subject matter of Examples 3-4 includes, wherein the EFB has an exterior wall that is tapered, stepped, or contoured, relative to the longitudinal axis.

In Example 6, the subject matter of Examples 1-5 includes, wherein the EFB facilitates articulation, contourability, and flaring of the polishing cup in response to applied forces along the longitudinal axis and also along an off-center axis that is offset from the longitudinal axis.

In Example 7, the subject matter of Examples 1-6 includes, wherein the certain distance from the distal end at which the EFB is situated is not greater than 0.7 times the distal diameter.

In Example 8, the subject matter of Example 7 includes, wherein the certain distance from the distal end at which the EFB is situated is about 0.55 times the distal diameter.

In Example 9, the subject matter of Examples 7-8 includes, wherein the certain distance from the distal end at which the EFB is situated is about 0.4 times the distal diameter.

In Example 10, the subject matter of Examples 1-9 includes, wherein the distal diameter is between 5 and 7 mm.

In Example 11, the subject matter of Examples 1-10 includes, wherein the dental polishing cup is formed such that, under an applied force of 150 to 1500 grams at the distal end against a working surface, the distal diameter flares outward by an amount of greater than 15%.

In Example 12, the subject matter of Example 11 includes, wherein the dental polishing cup is formed such that, under an applied force of 150 to 1500 grams at the distal end against a working surface, the distal diameter flares outward by an amount of greater than 25%.

In Example 13, the subject matter of Example 12 includes, wherein the dental polishing cup is formed such that, under an applied force of 150 to 1500 grams at the distal end against a working surface, the distal diameter flares outward by an amount of greater than 30%.

In Example 14, the subject matter of Example 13 includes, wherein the dental polishing cup is formed such that, under an applied force of 150 to 1500 grams at the distal end against a convex working surface having a radius of curvature that is between 0.45 and 0.38 times the distal diameter, the distal end conforms around the convex working surface to maintain contact along the entire circumference of the distal end.

In Example 15, the subject matter of Examples 1-14 includes, wherein the EFB facilitates articulation of the polishing cup in response to applied forces along an off-center axis that is offset from the longitudinal axis, up to an offset limit at which point the EFB closes to prevent such facilitated articulation.

In Example 16, the subject matter of Examples 1-15 includes, wherein the proximal end comprises a fastener.

In Example 17, the subject matter of Examples 1-16 includes, wherein the EFB comprises a plurality of circumferential grooves.

In Example 18, the subject matter of Examples 1-17 includes, wherein the body comprises a plurality of portions formed from different materials of different hardness, and wherein the EFB comprises a band of material which has a softer or more compressible material than the polishing-cup body portions immediately proximally, and immediately distally of the EFB.

In Example 19, the subject matter of Examples 1-18 includes, wherein the EFB comprises a plurality of perforations, portals, or cutouts in the body.

Example 20 is a dental kit, comprising: a power handle; a polishing cup head a polishing cup; and polishing paste; wherein the polishing cup, comprises: a body comprising an elastic material, the body having a length along a longitudinal axis, a proximal end, a distal end, and a round cross-section taken perpendicularly to the length, wherein the body has a distal diameter at the distal end, and the body further defines a cup cavity with an opening at the distal end; and wherein a portion of the body includes, an enhanced-flexibility band (EFB) situated circumferentially at a certain distance from the distal end, the EFB providing a lesser stiffness of the body than other portions of the body that are situated lengthwise immediately distally and immediately proximately of the EFB.

The embodiments above are intended to be illustrative and not limiting. Additional embodiments are within each claim that does not expressly exclude such subject matter. In addition, although aspects of the present invention have been described with reference to particular embodiments, those skilled in the art will recognize that changes may be made in form and detail without departing from the scope of the invention, as defined by the claims.

Persons of ordinary skill in the relevant arts will recognize that the invention may comprise fewer features than illustrated in any individual embodiment described above. The embodiments described herein are not meant to be an exhaustive presentation of the ways in which the various features of the invention may be combined. Accordingly, the embodiments are not mutually exclusive combinations of features; rather, the invention may comprise a combination of different individual features selected from different individual embodiments, as will be understood by persons of ordinary skill in the art.

What is claimed is:

1. A dental polishing cup for holding a dental treatment material, the polishing cup comprising:
    a body comprising an elastic material, the body having a length along a longitudinal axis, a proximal end, a distal end, and a round cross-section taken perpendicularly to the length, wherein the body has a distal diameter at the distal end, and the body further defines a cup cavity with an opening at the distal end; and
    wherein a portion of an exterior surface of the body defines an enhanced-flexibility band (EFB) situated circumferentially at a distance from the distal end, the EFB having an external circumferential groove with a certain depth along a radial direction, the EFB providing a lesser stiffness of the body than other portions of the body that are situated lengthwise immediately distally and immediately proximately of the EFB.

2. The dental polishing cup of claim 1, wherein the body comprises a circumferential wall having a certain wall thickness any given point along the length, and wherein the EFB has an external circumferential groove forming a reduced wall thickness than the other portions of the body that are situated lengthwise immediately distally and immediately proximately of the EFB.

3. The dental polishing cup of claim 1, wherein the depth along the radial direction is at least 0.5 mm.

4. The dental polishing cup of claim 1, wherein the EFB has an exterior wall that is tapered, stepped, or contoured, relative to the longitudinal axis.

5. The dental polishing cup of claim 1, wherein the EFB facilitates articulation, contourability, and flaring of the polishing cup in response to applied forces along the longitudinal axis and also along an off-center axis that is offset from the longitudinal axis.

6. The dental polishing cup of claim 1, wherein the certain distance from the distal end at which the EFB is situated is not greater than 0.7 times the distal diameter.

7. The dental polishing cup of claim 6, wherein the certain distance from the distal end at which the EFB is situated is about 0.55 times the distal diameter.

8. The dental polishing cup of claim 6, wherein the certain distance from the distal end at which the EFB is situated is about 0.4 times the distal diameter.

9. The dental polishing cup of claim 1, wherein the distal diameter is between 5 and 7 mm.

10. The dental polishing cup of claim 1, wherein the dental polishing cup is formed such that, under an applied force of the distal end against a working surface, the distal diameter flares outward by an amount of greater than 15%.

11. The dental polishing cup of claim 10, wherein the dental polishing cup is formed such that, under an applied force of the distal end against a convex working surface having a radius of curvature that is between 0.45 and 0.38 times the distal diameter, the distal end conforms around the convex working surface to maintain contact along the entire circumference of the distal end.

12. The dental polishing cup of claim 1, wherein the EFB facilitates articulation of the polishing cup in response to applied forces along an off-center axis that is offset from the longitudinal axis, up to an offset limit at which point the EFB closes to prevent such facilitated articulation.

13. The dental polishing cup of claim 1, wherein the proximal end comprises a fastener.

14. The dental polishing cup of claim 1, wherein the EFB comprises a plurality of circumferential grooves.

15. The dental polishing cup of claim 1, wherein the body comprises a plurality of portions formed from different materials of different hardness, and wherein the EFB comprises a band of material which has a softer or more compressible material than the polishing-cup body portions immediately proximally, and immediately distally of the EFB.

16. The dental polishing cup of claim 1, wherein the EFB comprises a plurality of perforations, portals, or cutouts in the body.

17. A dental kit, comprising:
    a power handle;
    a polishing cup; and
    polishing paste;
    wherein the polishing cup, comprises:
        a body comprising an elastic material, the body having a length along a longitudinal axis, a proximal end, a distal end, and a round cross-section taken perpendicularly to the length, wherein the body has a distal diameter at the distal end, and the body further defines a cup cavity for the polishing paste, with an opening at the distal end; and
    wherein a portion of an exterior surface of the body includes an enhanced-flexibility band (EFB) situated circumferentially at a distance from the distal end, the EFB having an external circumferential groove with a certain depth along a radial direction, the EFB providing a lesser stiffness of the body than other portions of the body that are situated lengthwise immediately distally and immediately proximately of the EFB.

18. The dental kit of claim 17, further comprising one or more of a charging unit, a brush head, a power supply, a scaler tool, a sanitizer unit, and a charging cradle.

19. The dental kit of claim 18, further comprising a polishing cup head connectable to the polishing cup.

* * * * *